| (12) | United States Patent | (10) Patent No.: US 12,417,819 B2 |
|---|---|---|
| | Ju | (45) Date of Patent: Sep. 16, 2025 |

(54) METHODS AND COMPOSITIONS FOR GERMLINE VARIANT DETECTION

(71) Applicant: Illumina, Inc., San Diego, CA (US)

(72) Inventor: Jin Hyun Ju, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1722 days.

(21) Appl. No.: 16/669,270

(22) Filed: Oct. 30, 2019

(65) Prior Publication Data

US 2020/0143905 A1 May 7, 2020

Related U.S. Application Data

(60) Provisional application No. 62/754,094, filed on Nov. 1, 2018.

(51) Int. Cl.
*G16B 20/20* (2019.01)
*G16B 30/10* (2019.01)

(52) U.S. Cl.
CPC ............. *G16B 20/20* (2019.02); *G16B 30/10* (2019.02)

(58) Field of Classification Search
None
See application file for complete search history.

(56) References Cited

U.S. PATENT DOCUMENTS

2018/0218789 A1   8/2018   Anderson

FOREIGN PATENT DOCUMENTS

| CN | 104662168 | 5/2015 |
|---|---|---|
| CN | 106459967 | 2/2017 |
| CN | 107491666 | 12/2017 |
| CN | 107779506 | 3/2018 |
| CN | 108350497 | 7/2018 |
| RU | 2442999 | 2/2012 |
| RU | 2589834 | 7/2016 |

OTHER PUBLICATIONS

Illumina et al., "Analysis of TMB and MSI Status with TruSight™ Oncology 500", Jul. 17, 2019 (Jul. 17, 2019), XP055664582, Retrieved from the Internet: URL: https://www.illumina.com/content/dam/illumina-marketing/documents/products/appnotes/trusightonocology-500-tmb-analysis-1170-2018-009.pdf.
Lek et al., "Analysis of protein-coding genetic variation in 60,706 humans", Nature, Aug. 18, 2016, vol. 536, pp. 285-291.
Illumina el al., "TruSight(TM) Oncology 500 A comprehensive nextgeneration sequencing assay that targets somatic variants, TMB, and MSI status from the same FFPE tumor only sample.", Jan. 9, 2019 (Jan. 9, 2019), XP055664586, Retrieved from the Internet: URL:http://albiogen-ru/upload/iblock/8e6/8e66914c1b78f53509fe9186d80f8d75.pdf.
Illumina et al., "TruSight Oncology 500 Local App: User Guide", Feb. 10, 2019 (Feb. 10, 2019), XP055664577, Retrieved from the Internet: URL: https://support.illumina.com/content/dam/illumina-support/documents/documentation/software_documentation/trusight-oncology-500/trusight-oncology-500-local-app-user-guide-1000000067616_03.pdf.
Zhang et al. "Comprehensive Evaluation of Illumina's TruSight Tumor 170 Panel to Estimate Tumor Mutational Burden", In: "AACR 2017", Apr. 1, 2017 (Apr. 1, 2017), Illumina, XP055486051.
Search Report and Written Opinion issued is patent application No. PCT/US2019/058895, mailed Feb. 12, 2020.

*Primary Examiner* — Joseph Woitach
(74) *Attorney, Agent, or Firm* — KNOBBE, MARTENS, OLSON & BEAR, LLP

(57) ABSTRACT

Some embodiments of the methods and systems provided herein relate to variant calling from sequence data obtained from a single sample. In some embodiments, a somatic variant can be distinguished from a germline variant based on variant allele frequency in a sample and location in a genome.

16 Claims, 8 Drawing Sheets

FFPE Specimens — Multiple tissue types supported

Sample Prep — Commercial DNA extraction kits

Library Prep and Enrichment
- TruSight™ Oncology + UMI kit
- DNA Probes - 523 genes

Sequencing
- NextSeq™ 500/550
- NextSeq™ 550Dx

Analysis
- Tumor Mutational Burden
- Microsatellite Instability
- Small DNA Variants

FIG. 5

METHODS AND COMPOSITIONS FOR GERMLINE VARIANT DETECTION

CROSS-REFERENCE TO RELATED APPLICATIONS

This application claims priority to U.S. Provisional Application No. 62/754,094, filed on Nov. 1, 2018, which is hereby incorporated by reference in its entirety.

FIELD OF THE INVENTION

Some embodiments of the methods and systems provided herein relate to variant calling from sequence data obtained from a single sample. In some embodiments, a somatic variant can be distinguished from a germline variant based on variant allele frequency of a variant in a sample and its location in a genome.

BACKGROUND OF THE INVENTION

DNA mutation is a cause of cancer and a focus of cancer research and treatment. Next-generation sequencing (NGS) is a promising technology for de novo mutation detection due to the huge number of reads that modern sequencers can generate. Theoretically, all mutations or variants in a genomic sample, regardless of the variant allele frequency (VAF) or genomic region, can be observed given enough read depth. However, calling variants with confidence is not trivial due to noise in the reads. Several bioinformatics tools have been developed to uncover variants from sequencing reads, and such procedures typically consist of three components: read processing, mapping and alignment, and variant calling.

For read processing, the low quality bases, usually near the 3' end of reads, and exogenous sequences such as sequencing adapters are trimmed from the DNA sample read processing tools. Second, the cleaned reads are mapped using mapping and alignment tools to determine where the variants may come from in a reference genome, and then aligned base-by-base. The third step, the process of variant calling is used to separate real variants from artifacts stemming from library preparation, sample enrichment, sequencing, and mapping/alignment. There is a continued need for improved methods of variant calling from sequence data.

SUMMARY OF THE INVENTION

Some embodiments include a method for identifying somatic variants in a plurality of variants, comprising: (a) obtaining a plurality of variants comprising somatic variants and germline variants; (b) applying a database filter to the plurality of variants, comprising: determining first germline variants in the plurality of variants, wherein the first germline variants each have an allele count in a first reference set of variants greater than or equal to a threshold allele count; (c) applying a proximity filter to the plurality of variants, comprising: (i) binning variants of the plurality of variants into a plurality of bins, wherein variants located in the same region of a genome are binned into the same bin, (ii) determining database variants in the plurality of variants, wherein a database variant is present in a second reference set of variants, and (iii) determining second germline variants in the plurality of variants, wherein the second germline variants each have an allele frequency within a proximate range of an allele frequency of at least one database variant in the same bin as the second germline variant; and (d) determining somatic variants in the plurality of variants by removing the identified first and second germline variants from the plurality of variants.

In some embodiments, (b) and (c) are performed consecutively.

In some embodiments, (c) is performed before (b).

In some embodiments, the threshold allele count is 5. In some embodiments, the threshold allele count is 10.

In some embodiments, the first and second reference set of variants are the same reference set.

In some embodiments, the first or second reference set of variants comprises a database of variants for a plurality of individuals. In some embodiments, the first or second reference set of variants comprises at least one database selected from a genome aggregation database (gnomAD), and a 1000 genome database.

In some embodiments, the same region of a genome is within the same chromosome. In some embodiments, the same region of a genome is within the same chromosomal arm. In some embodiments, the same region of a genome is within the same chromosomal cytoband. In some embodiments, the same region of a genome is within a 10 Mb region.

In some embodiments, the applying a proximity filter further comprises identifying a second germline variant having an allele frequency greater than or equal to 0.9.

In some embodiments, the applying a proximity filter further comprises identifying a second germline variant in the plurality of variants, wherein the second germline variant is a database variant present in the second reference set of variants.

In some embodiments, the proximate range is a range having a maximum and a minimum of 0.05 from the allele frequency of a second germline variant.

In some embodiments, the proximate range is a range having a maximum and a minimum of two standard deviations from a binomial distribution of an allele frequency of a second germline variant, and centered from the allele frequency of a second germline variant.

In some embodiments, the second germline variants have an allele frequency within a threshold proximity to an allele frequency of at least five database variants in the same bin as the second germline variant. In some embodiments, the second germline variants have an allele frequency within a threshold proximity to an allele frequency of at least ten database variants in the same bin as the second germline variant.

In some embodiments, (a) comprises: obtaining sequence data from a biological sample comprising a tumor cell. Some embodiments also include aligning the sequence data with a reference sequence, and identifying variants in the sequence data.

In some embodiments, the biological sample comprising a tumor cell is selected from a serum sample, a stool sample, a blood sample, a tumor sample. In some embodiments, the tumor sample is fixed.

Some embodiments include a method of determining a tumor mutation burden of a tumor, comprising: obtaining sequence data from a biological sample comprising a tumor cell; determining a plurality of variants from the sequence data; and determining the number of somatic variants in a plurality of variants according to the method of any one of the foregoing embodiments, wherein the number of somatic variants is the tumor mutation burden of the tumor.

Some embodiments include a method of treating a tumor, comprising: determining a tumor having a tumor mutation burden greater than or equal to 10 somatic variants according to a method of determining a tumor mutation burden of a tumor; and treating the tumor by administering an effective amount of a checkpoint inhibitor.

In some embodiments, the tumor is selected from the group consisting of a colorectal tumor, a lung tumor, an endometrium tumor, a uterine tumor, a gastric tumor, a melanoma, a breast tumor, a pancreatic tumor, a kidney tumor, a bladder tumor, and a brain tumor.

In some embodiments, the checkpoint inhibitor is selected from the group consisting of a CTLA-4 inhibitor, a PD-1 inhibitor, and a PD-L1 inhibitor. In some embodiments, the checkpoint inhibitor is selected from the group consisting of Ipilimumab, Nivolumab, Pembrolizumab, Spartalizumab, Atezolizumab, Avelumab, and Durvalumab.

Some embodiments include an electronic system for analyzing genetic variation data, comprising: an informatics module running on a processor and adapted to identify a plurality of variants from sequence data from a biological sample comprising a tumor cell, wherein the plurality of variants comprises somatic variants and germline variants; a database filter module adapted to remove first germline variants from the plurality of variants, wherein the first germline variants each have an allele count in a first reference set of variants greater than or equal to a threshold allele count; a proximity filter module adapted to remove second germline variants from the plurality of variants, the proximity filter module comprising: a binning sub-module adapted to return a plurality of bins, each bin containing variants of the plurality of variants located in the same region of a genome, an identification sub-module adapted to return database variants in the plurality of variants, wherein a database variant is present in a second reference set of variants, and a removal sub-module adapted to remove second germline variants from the plurality of variants, wherein the second germline variants each have an allele frequency within a proximate range of an allele frequency of at least one database variant in the same bin as the second germline variant; and a display module adapted to return variants not removed from the plurality of variants.

In some embodiments, informatics module comprises a variant annotation tool.

In some embodiments, the threshold allele count is 5. In some embodiments, the threshold allele count is 10.

In some embodiments, the first and second reference set of variants are the same reference set.

In some embodiments, the first or second reference set of variants comprises a database of variants for a plurality of individuals. In some embodiments, the first or second reference set of variants comprises at least one database selected from a genome aggregation database (gnomAD), and a 1000 genome database.

In some embodiments, the same region of a genome is within the same chromosome. In some embodiments, the same region of a genome is within the same chromosomal arm. In some embodiments, the same region of a genome is within the same chromosomal cytoband. In some embodiments, the same region of a genome is within a 10 Mb region.

In some embodiments, the removal sub-module is adapted to remove a variant having an allele frequency greater than or equal to 0.9 from the plurality of variants.

In some embodiments, the removal sub-module is adapted to remove a database variant present in the second reference set of variants from the plurality of variants.

In some embodiments, the proximate range is a range having a maximum and a minimum of 0.05 from the allele frequency of a second germline variant.

In some embodiments, the proximate range is a range having a maximum and a minimum of two standard deviations from a binomial distribution of an allele frequency of a second germline variant, and centered from the allele frequency of a second germline variant.

In some embodiments, the second germline variants have an allele frequency within a threshold proximity to an allele frequency of at least five database variants in the same bin as the second germline variant. In some embodiments, the second germline variants have an allele frequency within a threshold proximity to an allele frequency of at least ten database variants in the same bin as the second germline variant.

In some embodiments, the biological sample comprising a tumor cell is selected from a serum sample, a stool sample, a blood sample, a tumor sample. In some embodiments, the tumor sample is fixed.

Some embodiments include a computer-implemented method for identifying somatic variants in a plurality of variants, comprising: performing the method of any one of the foregoing methods.

Some embodiments include a computer-implemented method for identifying somatic variants in a plurality of variants, comprising: (a) receiving a plurality of variants from sequence data from a biological sample comprising a tumor cell, the plurality of variants comprising somatic variants and germline variants; (b) applying a database filter to the plurality of variants, comprising: creating an index of documents for the plurality of variants, searching a first reference set of variants with the index to identify first germline variants in the index, wherein the first germline variants each have an allele count in the first reference set of variants greater than or equal to a threshold allele count, and removing the identified first germline variants from the index to create an index of first filtered variants; (c) applying a proximity filter to the index of first filtered variants, comprising: (i) creating a plurality of bins for different regions of a genome, (ii) binning variants of the index of first filtered variants, wherein variants located in the same region of a genome are binned into the same bin, (iii) searching a second reference set of variants with the index of first filtered variants to identify database variants in the index of first filtered variants, (iii) generating an index of second germline variants from the index of first filtered variants by identifying second germline variants, wherein the second germline variants each have an allele frequency within a proximate range of an allele frequency of at least one database variant in the same bin as the second germline variant, and (iv) removing the identified second germline variants from the index of first filtered variants to create an index of somatic variants, thereby identifying somatic variants in the plurality of variants.

In some embodiments, the threshold allele count is 5. In some embodiments, the threshold allele count is 10.

In some embodiments, the first and second reference set of variants are the same reference set.

In some embodiments, the first or second reference set of variants comprises a database of variants for a plurality of individuals. In some embodiments, the first or second reference set of variants comprises at least one database selected from a genome aggregation database (gnomAD), and a 1000 genome database.

In some embodiments, the same region of a genome is within the same chromosome. In some embodiments, the same region of a genome is within the same chromosomal arm. In some embodiments, the same region of a genome is within the same chromosomal cytoband. In some embodiments, the same region of a genome is within a 10 Mb region.

In some embodiments, the generating an index of second filtered variants further comprises identifying a second germline variant having an allele frequency greater than or equal to 0.9.

In some embodiments, the generating an index of second filtered variants further comprises identifying a second germline variant in the plurality of variants, wherein the second germline variant is a database variant present in the second reference set of variants.

In some embodiments, the proximate range is a range having a maximum and a minimum of 0.05 from the allele frequency of a second germline variant.

In some embodiments, the proximate range is a range having a maximum and a minimum of two standard deviations from a binomial distribution of an allele frequency of a second germline variant, and centered from the allele frequency of a second germline variant.

In some embodiments, the second germline variants have an allele frequency within a threshold proximity to an allele frequency of at least five database variants in the same bin as the second germline variant. In some embodiments, the second germline variants have an allele frequency within a threshold proximity to an allele frequency of at least ten database variants in the same bin as the second germline variant.

In some embodiments, the biological sample comprising a tumor cell is selected from a serum sample, a stool sample, a blood sample, a tumor sample. In some embodiments, the tumor sample is fixed.

BRIEF DESCRIPTION OF THE DRAWINGS

FIG. 5 depicts an overview of an example embodiment of a workflow that includes obtaining formalin-fixed paraffin embedded (FFPE) samples, obtaining sequence data, and analyzing the sequence data.

DETAILED DESCRIPTION

Figure 1:
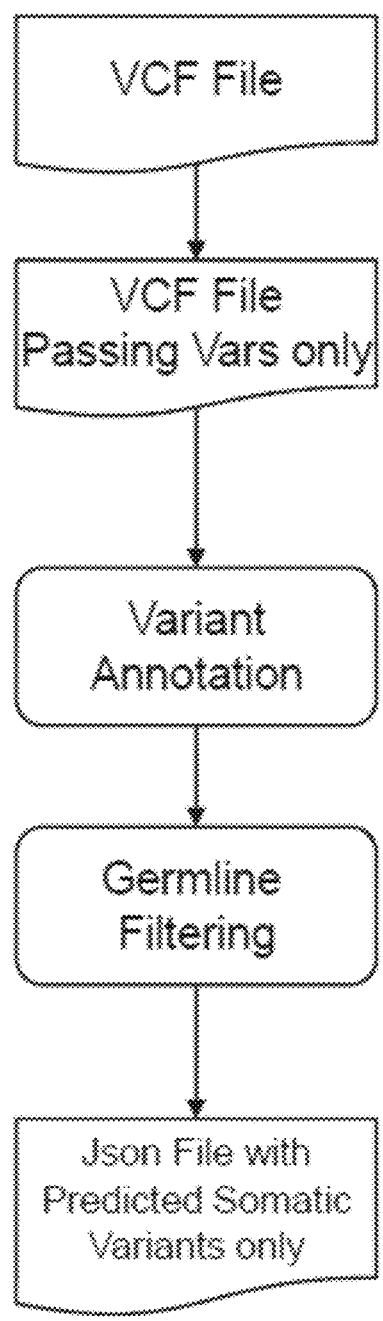
FIG. 1 depicts an example embodiment of a workflow that includes obtaining sequence data, such as a VCF file, identifying and annotating variants in the data, identifying and filtering germline variant, and returning a variant table indicating the status of the variants.

Some embodiments of the methods and systems provided herein relate to variant calling from sequence data obtained from a single sample. In some embodiments, a somatic variant can be distinguished from a germline variant based on the variant's allele frequency in a sample and the variant's location in a genome. As used herein, a "variant" can include a polymorphism within a nucleic acid molecule. A polymorphism can include an insertion, deletion, variable length tandem repeats, single nucleotide mutation, and a structural variant such as translocation, copy number variation, or a combination thereof. As used herein, a "germline variant" can include a variant present in germ cells and all cells of an individual. As used herein, a "somatic variant" can include a variant present in a tumor cell, and not in other cells of an individual.

Traditionally, variant calling between somatic variants and germline variants has relied on a comparison between data obtained from a tumor sample, and data obtained from a matched normal sample. However, traditional variant calling requires a matched sample to be available, and for two sets of data to be obtained. Embodiments provided herein relate to variant calling from sequence data taken from a single sample from an individual. Using a single sample may reduce the need for a matched sample, and the costs that would have been required for obtaining sequence data for both a tumor sample, and a matched normal sample.

Some embodiments relate to obtaining sequence data from a sample, such as a sample from an individual comprising a tumor cell, comparing the sequence data to a reference to identify a plurality of variants in the sequence data, and applying one or more filters to the variants to identify germline variants and somatic variants. In some embodiments, a filter can include a proximity filter. In some embodiments, the proximity filter includes binning the plurality of variants into a plurality of bins according to the location of the variants in a genome. Some of the binned variants can be identified as germline variants by the presence of corresponding variants in one or more reference sets of variants. An uncharacterized binned variant can be determined to be a germline variant if the uncharacterized binned variant has an allele frequency similar to the allele frequency of one or more identified germline variants in the same bin as the uncharacterized variant. Some embodiments also include applying a database filter to identify germline variants. The database filter can identify germline variants according to an allele count of corresponding variants in one or more reference sets of variants. In some embodiments, a database filter and a proximity filter can be applied to the plurality of variants to identify germline variants. In some embodiments, somatic variants are variants that are identified as germline variants. The number of somatic variants can indicate the tumor mutation burden of a tumor.

Tumor mutation burden has emerged as an important biomarker for cancer therapy selection after recent studies have shown a correlation between tumor mutation burden and the effectiveness of checkpoint inhibitor immunotherapies. In calculating the tumor mutation burden, it is useful to identify and filter out germline variants. The germline variants may include variants that an individual is born with (or shared between the tumor and the normal cell) but which are detected as variants in comparison to the reference genome. These variants do not contribute to distinguishing tumor cells from normal cells, and thus can lead to over estimation of the tumor mutation burden if not correctly filtered out. Embodiments include determining a tumor mutation burden for a tumor, selecting a treatment for the tumor according to the tumor mutation burden, and administering the treatment to a subject in need thereof.

Certain Methods

Some embodiments of the methods and systems provided herein relate to a method for identifying a somatic variant in a plurality of variants comprising somatic variants and germline variants. In some embodiments, germline variants can be filtered from the plurality of variants using one or more filters. Examples of such filters include a database filter, and a proximity filter.

In some embodiments, a database filter can be applied to a plurality of variants. The database filter can be used to identify a variant as a germline variant, and remove the variant from the plurality of variants. The database filter can be related to an allele count of a corresponding variant in a database, for a particular variant of the plurality of variants.

For each variant in the plurality, a reference database can be searched for the corresponding variant in the database. A reference database can include a database of variants for a plurality of individuals. Examples of databases useful with embodiments provided herein include a genome aggregation database (gnomAD), including gnomAD exome and gnomAD genome databases, and a 1000 genome database (International Genome Sample Resource). See e.g., Lek, M., et al., (2016) Nature 536:285-292 which is incorporated by reference in its entirety. A total allele count can be determined for the corresponding variant in one or more reference databases. An allele count can represent the total number of observations within a database that a variant is observed. For example, an allele count of 10 in a database for a corresponding variant denotes that the corresponding variant has been observed in at least 5 samples for homozygous variants, or a maximum of 10 samples for heterozygous variants. In some embodiments, an allele count can be the highest allele count observed in more than one databases. A variant having a corresponding variant with an allele count greater than or equal to a certain threshold allele count can be identified as a germline variant In some embodiments, the threshold allele count can be greater than or equal to 2, 3, 4, 5, 6, 7, 8, 9, 10, 11, 12, 13, 14, 15, 16, 17, 18, 19 and 20.

In some embodiments, a proximity filter can be applied to a plurality of variants. The database filter can be used to identify a variant as a germline variant, and remove the variant from the plurality of variants. The proximity filter can be related to the allele frequency of a certain variant of the plurality of variants, the location of the variant in region of a genome, and the proximity of the allele frequency of the variant to the allele frequency of identified germline variants in the same region of a genome. In some embodiments, variants of the plurality of variants can be sorted or binned into a plurality of bins, such that variants located in the same region of a genome are sorted or binned into the same bin. In some embodiments, the same region of a genome can be within the same chromosome, within the same arm of a chromosome, within the same chromosomal cytoband. In some embodiments, the same region of a genome can be within the same contiguous 100 Mb, 50 Mb, 40 Mb, 30 Mb, 20 Mb, 10 Mb, 5 Mb, 1 Mb, or within any range between any two of the foregoing numbers.

In some embodiments, the proximity filter also includes determining which binned variants are readily identifiable as germline variants. For example, a binned variant can have a corresponding variant present in one or more reference databases and be identified as a germline variant.

In some embodiments, the proximity filter includes determining that variants having an allele frequency greater than or equal to a threshold frequency in the sample are germline variants. In some such embodiments, variants having an allele frequency greater than or equal to 0.7, 0.8, 0.9, or 1.0 can be identified as germline variants.

In some embodiments, the proximity filter includes determining a proximate range of an allele frequency for a variant that has not been identified as a germline variant. A proximate range of an allele frequency for a variant can include a range of allele frequencies above and below the allele frequency of the variant. In some embodiments, the proximate range is a range having a maximum and a minimum from the allele frequency of variant of 0.01, 0.02, 0.03, 0.04, 0.05, 0.06, 0.07, 0.08, 0.09, or any number within a range between any two of the foregoing numbers. For example, for a variant having an allele frequency of 0.2 and a proximate range of 0.05, the minimum and maximum of the proximate range would be allele frequencies of 0.15 and 0.25, respectively.

In some embodiments, the proximate range is determined by the value of two (n) standard deviations of a binomial distribution assuming the supporting evidence for the given variant is generated by a binomial process. For example, for a variant having an allele frequency (x), with a coverage (y), the proximate range (z) can be:

$$z = n*\mathrm{sqrt}(y*x*(1-x))/y$$

For example, for a variant having an allele frequency of 0.2, a coverage/depth of sequencing of 100, the proximate range would be 0.08, and the minimum and maximum of the proximate range would be allele frequencies of 0.12 and 0.28, respectively. In some embodiments, the proximate range is the higher of either 0.05, or two (n) standard deviations from a binomial distribution of the allele frequency of the variant, above and below the allele frequency of the variant.

In some embodiments, a variant can be identified as a germline variant if the variant has an allele frequency within proximate range of one or more identified germline variants in the same bin as the variant. In some embodiments, a variant can be identified as a germline variant if the variant has an allele frequency within proximate range of more than 1, 2, 3, 4, 5, 6, 7, 8, 9, or 10 identified germline variants in the same bin as the variant. In some embodiments, a variant can be identified as a germline variant if the variant has an allele frequency within proximate range of more than 5 identified germline variants in the same bin as the variant. For example, in an embodiment in which a variant would be identified as a germline variant if the variant has an allele frequency within proximate range of more than 5 identified germline variants in the same bin as the variant: a variant having an allele frequency of 0.2, with a proximate range of 0.05, thus having a minimum range of 0.15 and a maximum range of 0.25 and binned in a bin representing chromosome 7 would be identified as a germline variant where more than 5 identified germline variants having allele frequencies in proximate range of the variant and binned in the bin representing chromosome 7.

In some embodiments, the proximity filter identifies somatic variants which are variants not identified as germline variants. In some embodiments, the number of somatic variants obtained from sequencing data from a tumor is the tumor mutation burden of the tumor.

In some embodiments, the database filter or the proximity filter can be applied to the plurality of variants to identify and remove germline variants from the plurality of variants. In some embodiments, the database filter and the proximity filter can be applied consecutively. For example, the output of the database filter such can be used for the input of the proximity filter. Conversely, the output of the proximity filter can be used as the input of the database filter.

Certain Electronic Systems and Computer-Implemented Methods

Some embodiments of the methods and systems provided herein include electronic system for analyzing genetic variation data. In some such embodiments, a database filter described herein and/or a proximity filter described herein can be applied to the genetic variation data to identify germline variants.

Some embodiments can include an informatics module running on a processor and adapted to identify a plurality of variants from sequence data from a biological sample comprising a tumor cell, in which the plurality of variants comprises somatic variants and germline variants.

Some embodiments include a database filter module adapted to remove germline variants from the plurality of variants, wherein the germline variants each have an allele count in a reference set of variants greater than or equal to a threshold allele count. In some embodiments, the threshold allele count can be greater than or equal to 2, 3, 4, 5, 6, 7, 8, 9, 10, 11, 12, 13, 14, 15, 16, 17, 18, 19 and 20.

Some embodiments include a proximity filter module adapted to remove germline variants from the plurality of variants. In some embodiments, the proximity filter module can include a binning sub-module adapted to return a plurality of bins, each bin containing variants of the plurality of variants located in the same region of a genome. In some embodiments, variants of the plurality of variants can be sorted or binned into a plurality of bins, such that variants located in the same region of a genome are sorted or binned into the same bin. In some embodiments, the same region of a genome can be within the same chromosome, within the same arm of a chromosome, within the same chromosomal cytoband. In some embodiments, the same region of a genome can be within the same contiguous 100 Mb, 50 Mb, 40 Mb, 30 Mb, 20 Mb, 10 Mb, 5 Mb, 1 Mb, or within any range between any two of the foregoing numbers.

In some embodiments, the proximity filter module can include an identification sub-module adapted to return database variants in the plurality of variants, wherein a database variant is present in a reference set of variants.

In some embodiments, the proximity filter module can include a removal sub-module adapted to remove germline variants from the plurality of variants, wherein the germline variants each have an allele frequency within a proximate range of an allele frequency of at least one database variant in the same bin as the germline variant. In some embodiments, the proximity filter includes determining a proximate range of an allele frequency for a variant that has not been identified as a germline variant. In some embodiments, the approximate range is a range having a maximum and a minimum from the allele frequency of a variant of 0.01, 0.02, 0.03, 0.04, 0.05, 0.06, 0.07, 0.08, 0.09, or any number within a range between any two of the foregoing numbers. In some embodiments, the proximate range is a range having a maximum and a minimum of two standard deviations from a binomial distribution of the allele frequency of the variant. In some embodiments, the proximate range is the higher of 0.05, or two (n) standard deviations from a binomial distribution of the allele frequency of the variant, above and below the allele frequency of the variant.

In some embodiments, a variant can be identified as a germline variant if the variant has an allele frequency within proximate range of one or more identified germline variants in the same bin as the variant. In some embodiments, a variant can be identified as a germline variant if the variant has an allele frequency within proximate range of more than 1, 2, 3, 4, 5, 6, 7, 8, 9, or 10 identified germline variants in the same bin as the variant. In some embodiments, the removal sub-module is adapted to remove a variant having an allele frequency greater than or equal to a threshold frequency. In some such embodiments, variants having an allele frequency greater than or equal to 0.7, 0.8, 0.9, or 1.0 can be identified as germline variants. In some embodiments, the removal sub-module is adapted to remove a database variant present in the reference set of variants from the plurality of variants.

Some embodiments provided herein include computer-implemented methods for identifying somatic variants in a plurality of variants. Some such embodiments can include receiving a plurality of variants from sequence data from a biological sample comprising a tumor cell, the plurality of variants can include somatic variants and germline variants.

Some embodiments include applying a database filter to the plurality of variants. Some such embodiments include creating an index of documents for the plurality of variants, searching a reference set of variants with the index to identify germline variants in the index. In some embodiments, the germline variants each have an allele count in the reference set of variants greater than or equal to a threshold allele count. In some embodiments, the threshold allele count can be greater than or equal to 2, 3, 4, 5, 6, 7, 8, 9, 10, 11, 12, 13, 14, 15, 16, 17, 18, 19 and 20. Some embodiments also include removing the identified germline variants from the index to create an index of first filtered variants.

Some embodiments include applying a proximity filter to the index of first filtered variants. Some such embodiments include creating a plurality of bins for different regions of a genome. Some embodiments include binning variants of the index of first filtered variants, wherein variants located in the same region of a genome are binned into the same bin. In some embodiments, the same region of a genome can be within the same chromosome, within the same arm of a chromosome, within the same chromosomal cytoband. In some embodiments, the same region of a genome can be within the same contiguous 100 Mb, 50 Mb, 40 Mb, 30 Mb, 20 Mb, 10 Mb, 5 Mb, 1 Mb, or within any range between any two of the foregoing numbers.

Some embodiments include searching a reference set of variants with the index of first filtered variants to identify database variants in the index of first filtered variants.

Some embodiments include generating an index of germline variants from the index of first filtered variants by identifying germline variants. In some embodiments, the germline variants each have an allele frequency within a proximate range of an allele frequency of at least one database variant in the same bin as the second germline variant. In some embodiments, the proximate range is a range having a maximum and a minimum from the allele frequency of variant of 0.01, 0.02, 0.03, 0.04, 0.05, 0.06, 0.07, 0.08, 0.09, or any number within a range between any two of the foregoing numbers. In some embodiments, the proximate range is a range having a maximum and a minimum of two standard deviations from a binomial distribution of the allele frequency of the variant. In some embodiments, the proximate range is the higher of 0.05, or two (n) standard deviations from a binomial distribution of the allele frequency of the variant, above and below the allele frequency of the variant.

In some embodiments, a variant can be identified as a germline variant if the variant has an allele frequency within a proximate range of one or more identified germline variants in the same bin as the variant. In some embodiments, a variant can be identified as a germline variant if the variant has an allele frequency within proximate range of more than 1, 2, 3, 4, 5, 6, 7, 8, 9, or 10 identified germline variants in the same bin as the variant. In some embodiments, the germline variant can be identified as a variant having an allele frequency greater than or equal to a threshold frequency. In some such embodiments, variants having an allele frequency greater than or equal to 0.7, 0.8, 0.9, or 1.0 can be identified as germline variants.

Some embodiments include removing the identified germline variants from the index of first filtered variants to create an index of somatic variants, thereby identifying somatic variants in the plurality of variants. In some embodiments, the number of somatic variants obtained from sequencing data from a tumor is the tumor mutation burden of the tumor.

Methods of Treatment

Some embodiments of the methods and systems include methods of treating a tumor. In some such embodiments, the number of somatic variants present in a tumor can be determined by the methods and systems provided herein. For example, sequence data can be obtained from a tumor, a plurality of variants can be identified from the sequence data, and germline variants can be identified and removed from a plurality of variants, thereby identifying somatic variants in the plurality of variants. In some embodiments, germline variants can be identified and removed from the plurality of variants by applying one or more of a database filter, and/or a proximity filter, thereby identifying somatic variants that are not removed by applying the one or more of the filters. In some embodiments, the number of somatic variants obtained from sequencing data from a tumor is the tumor mutation burden of the tumor. In some embodiments, tumor mutation burden is calculated as an average number of somatic variants per genomic region, such as, for example, mutations per 50 kb, 100 kb, 1 Mb, 10 Mb, 100 Mb, and the like. Tumor mutation burden can be sampled by sequencing an entire genome or a portion thereof. For example, a portion of a genome may be sequenced by enriching for one or more genomic regions of interest, such as a tumor gene panel, a full exome, a partial exome, and the like.

Some embodiments of treating a tumor can include determining a tumor has a tumor mutation burden greater than or equal to a tumor mutation burden threshold, and contacting the tumor with an effective amount of therapeutic agent. Some embodiments include treating a subject having a tumor and can include determining a tumor has a tumor mutation burden greater than or equal to a TMB threshold, and administering to the subject an effective amount of therapeutic agent. In some embodiments, a tumor mutation burden threshold can be 2, 3, 4, 5, 6, 7, 8, 9, 10, 15, 20, 30, 40, 50, 60, 70, 80, 90, 100, 200, 300, 400, 500, 600, 700, 800, 900, 1000 or any number in a range between any two of the foregoing numbers. Examples of therapeutic agents include chemotherapeutic agents. In some embodiments, the therapeutic agent can include a checkpoint inhibitor. Examples of checkpoint inhibitors include a CTLA-4 inhibitor, a PD-1 inhibitor, and a PD-L1 inhibitor. In some embodiments, the checkpoint inhibitor can include Ipilimumab, Nivolumab, Pembrolizumab, Spartalizumab, Atezolizumab, Avelumab, and Durvalumab. Examples of tumors include a colorectal tumor, a lung tumor, an endometrium tumor, a uterine tumor, a gastric tumor, a melanoma, a breast tumor, a pancreatic tumor, a kidney tumor, a bladder tumor, and a brain tumor. More examples of cancers that can be treated with the methods and systems included herein are listed in U.S. 20180218789 which is expressly incorporated by reference herein in its entirety.

Samples

Some embodiments include obtaining sequence data from a biological sample. In some embodiments, a biological sample can include a tumor cell. In some embodiments, a biological sample can include a serum sample, a stool sample, a blood sample, and a tumor sample. In some embodiments, the biological sample is fixed.

In some embodiments, a subject can provide a biological sample. The biological sample can be any substance that is produced by the subject. Generally, the biological sample is any tissue taken from the subject or any substance produced by the subject. Examples of biological samples can include blood, plasma, saliva, cerebrospinal fluid (CSF), cheek tissue, urine, feces, skin, hair, organ tissue. In some embodiments, the biological sample is a solid tumor or a biopsy of a solid tumor. In some embodiments, the biological sample is a formalin-fixed, paraffin-embedded (FFPE) tissue sample. The biological sample can be any biological sample that comprises nucleic acids. Biological samples may be derived from a subject. The subject may be a mammal, a reptile, an amphibian, an avian, or a fish. Examples of mammals include a human, ape, orangutan, monkey, chimpanzee, cow, pig, horse, rodent, bird, reptile, dog, cat, dolphin, or other animal. Examples of reptiles include a lizard, snake, alligator, turtle, crocodile, iguana, and tortoise. Examples of amphibians include a toad, frog, newt, and salamander. Examples of avians include chickens, ducks, geese, penguins, ostriches, puffins, and owls. Examples of fish include catfish, eels, sharks, goldfish, and swordfish. In some embodiments, the subject is a human.

Certain Systems and Methods

Some embodiments include computer-based systems and computer implemented methods for performing the methods described herein. In some embodiments, the systems can be utilized for determining and reporting the presence or absence of variants in a sample, such as germline variants and/or somatic variants. The system can comprise one or more client components. The one or more client components can comprise a user interface. The system can comprise one or more server components. The server components can comprise one or more memory locations. The one or more memory locations can be configured to receive a data input. The data input can comprise sequencing data. The sequencing data can be generated from a nucleic acid sample from a subject. The system can further comprise one or more computer processor. The one or more computer processor can be operably coupled to the one or more memory locations. The one or more computer processor can be programmed to map the sequencing data to a reference sequence. The one or more computer processor can be further programmed to determine a presence or absence of a plurality of variants from the sequencing data. The one or more computer processor can be further programmed to apply at least one filter to the genetic variants to identify germline variants. Examples of filters include a database filter and a proximity filter. The one or more computer processor can be further programmed to remove identify germline variants from an index of the identified variants. The one or more computer processor can be further programmed to generate an output for display on a screen. The output can comprise one or more reports identifying the germline variants and/or the somatic variants in the plurality of variants.

Some embodiments of the methods and systems can comprise one or more client components. The one or more client components can comprise one or more software components, one or more hardware components, or a combination thereof. The one or more client components can access one or more services through one or more server components. The one or more services can be accessed by the one or more client components through a network. "Services" is used herein to refer to any product, method, function, or use of the system. For example, a user can place an order for a genetic test. The order can be placed through the one or more client components of the system and the request can be transmitted through a network to the one or more server components of the system. The network can be the Internet, an internet and/or extranet, or an intranet and/or extranet that is in communication with the Internet. The network in some cases is a telecommunication and/or data network. The network can include one or more computer servers, which can enable distributed computing, such as cloud computing. The network, in some cases with the aid of the computer system, can implement a peer-to-peer network, which may enable devices coupled to the computer system to behave as a client or a server.

Some embodiments of the systems can comprise one or more memory locations, such as random-access memory, read-only memory, flash memory, electronic storage unit, such as hard disk; communication interface, such as network adapter, for communicating with one or more other systems, and peripheral devices, such as cache, other memory, data storage and/or electronic display adapters. The memory, storage unit, interface and peripheral devices are in communication with the CPU through a communication bus, such as a motherboard. The storage unit can be a data storage unit or data repository for storing data. In one example, the one or more memory locations can store the received sequencing data.

Some embodiments of the methods and systems can comprise one or more computer processors. The one or more computer processors may be operably coupled to the one or more memory locations to e.g., access the stored sequencing data. The one or more computer processors can implement machine executable code to carry out the methods described herein. For instance, the one or more computer processors can execute machine readable code to map a sequencing data input to a reference sequence, and/or identify germline variants and/or somatic variants.

Some embodiments of the methods and systems provided herein can include machine executable or machine readable code. In some such embodiments, the machine executable or machine readable code can be provided in the form of software. During use, the code can be executed by the processor. In some cases, the code can be retrieved from the storage unit and stored on the memory for ready access by the processor. In some embodiments, the electronic storage unit can be precluded, and machine-executable instructions are stored on memory. The code can be pre-compiled and configured for use with a machine having a processor adapted to execute the code, can be compiled during runtime, or can be interpreted during runtime. The code can be supplied in a programming language that can be selected to enable the code to execute in a pre-compiled, as-compiled or interpreted fashion.

Some embodiments of the systems and methods provided herein, such as the computer system, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Some embodiments of the methods and systems disclosed herein can include or be in communication with one or more electronic displays. The electronic display can be part of the computer system, or coupled to the computer system directly or through the network. The computer system can include a user interface (UI) for providing various features and functionalities disclosed herein. Examples of UIs include, without limitation, graphical user interfaces(GUIs) and web-based user interfaces. The UI can provide an interactive tool by which a user can utilize the methods and systems described herein. By way of example, a UI as envisioned herein can be a web-based tool by which a healthcare practitioner can order a genetic test, customize a list of genetic variants to be tested, and receive and view a biomedical report.

Some embodiments of the methods and systems disclosed herein may comprise biomedical databases, genomic databases, biomedical reports, disease reports, case-control analysis, and rare variant discovery analysis based on data and/or information from one or more databases, one or more assays, one or more data or results, one or more outputs based on or derived from one or more assays, one or more outputs based on or derived from one or more data or results, or a combination thereof.

EXAMPLES

Example 1—Identifying Somatic Variants by Sample Comparison

Figure 2A:
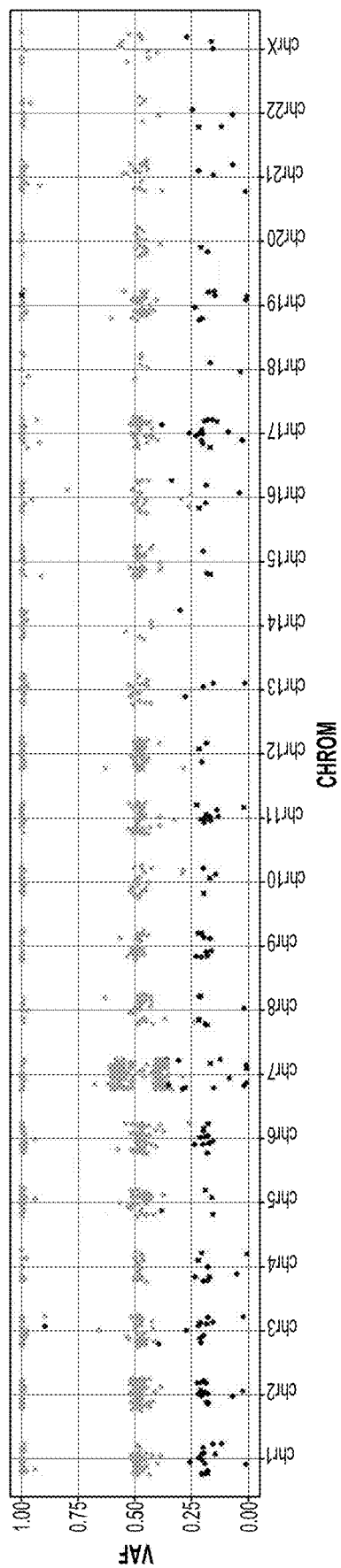
FIG. 2A is a graph showing the variant allele frequency (VAF) for various variants according to chromosomal location of each variant with somatic variants (black-filled circles), and germline variants (gray-filled circles).

Sequence data was obtained for a tumor sample and a normal sample from an individual. Variants were identified in the sequence data. Germline variants in the tumor sample were identified by comparing variants present in the tumor sample, and not the normal sample. FIG. 2A is a graph showing the variant allele frequency (VAF) for different variants according to chromosomal location of each variant with somatic variants (black-filled circles), and germline variants (gray-filled circles). This method required two samples from the individual.

Example 2—Database Filtering of Variants

Sequence data was obtained for a tumor sample only from Example 1. Variants were identified in the sequence data. In brief, variants called from a variant calling pipeline were annotated using an annotation tool, Nirvana (Illumina, San Diego). Nirvana provided clinical-grade annotation of genomic variants, such as single nucleotide variants, multi-nucleotide variants, insertions, deletions, copy number variants. The input to Nirvana was in a variant call format (VCF) and the output was a structured JSON representation of all annotation and sample information.

Figure 2B:
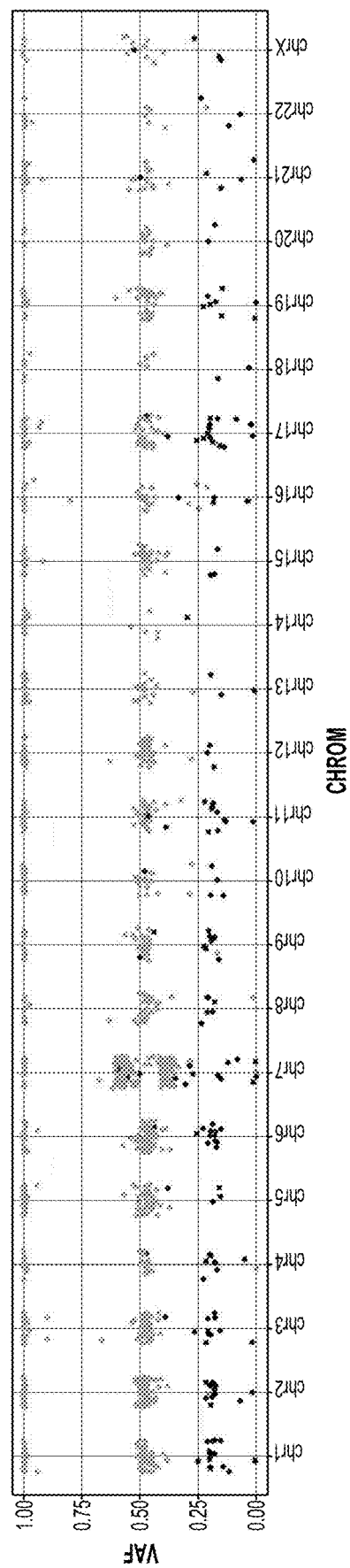
FIG. 2B is a graph showing the VAF for various variants according to chromosomal location of each variant with filter-determined somatic variants (black-filled circles), and filter-determined germline variants (gray-filled circles).

For identified variants, the total allele counts were parsed for a given variant in the genome aggregation database (gnomAD) exome, gnomAD genome, and the 1000 genome database along with the variant allele frequencies and coverage. These total allele counts represented the total number of observations within the database across different subpopulations. For each variant, the maximum allele count observed in all three databases was taken to take into account regions that were not covered in the exome database, while taking advantage of its larger sample size compared to the genome database. The filtering strategy marked variants with a maximum allele count of greater or equal than 10 as potential germline variants. An allele count of 10 in the database for a given variant means that it had been observed in at least 5 samples if they were all homozygous, or a maximum of 10 samples if they were all heterozygous. FIG. 2B is a graph showing the variant allele frequency (VAF) for various variants according to chromosomal location of each variant with filter-determined somatic variants (black-filled circles), and filter-determined germline variants (gray-filled circles). This demonstrated that database filtering only, mis-called variants.

Example 3—Proximity Filtering of Variants

Sequence data was obtained for a tumor sample only from an individual. Variants were identified in the sequence data. The database filter of Example 2 was applied to the variants. A proximity filter was used to further filter out variants that were not found in the database.

The proximity filter used information of database filtered variants in close positional proximity. For a given variant that was not found in the database and had an allele frequency lower than 0.9, variants on the same chromosome were retrieved within a given range of variant allele frequencies of the unfiltered variant. Variants with an allele frequency greater than 90% were marked as germline without any further processing. The range was determined as the maximum of 0.05 and 2 standard deviations of a binomial distribution assuming the supporting evidence for the given variant is generated by a binomial process. For example, if the unfiltered variant had an allele frequency of 0.2 with coverage of 100, the range was the maximum between 0.05 and $2*\mathrm{sqrt}(100*0.2*(1-0.2))/100=0.08$, which was 0.08. This translated into a range of 0.08 in both directions, and all variants were retrieved from the same chromosome with allele frequencies between 0.12 and 0.28. Subsequently, the number of retrieved variants exceed a fixed threshold was checked, this was set at 5. If the number of variants required was met, we then checked whether a significant fraction, which was set at 0.95, of those variants were filtered by the database filter. A variant was marked by the proximity filter if it met both conditions. In other words, if a variant was surrounded by a sufficient number of variants in the allele frequency space that were found in the database, it was considered a germline variant as well. This filter removed germline variants in normal regions with expected variant allele frequencies around 50% or 100%, and in copy number variant regions where the allele frequency distribution might be shifted.

Figure 3:
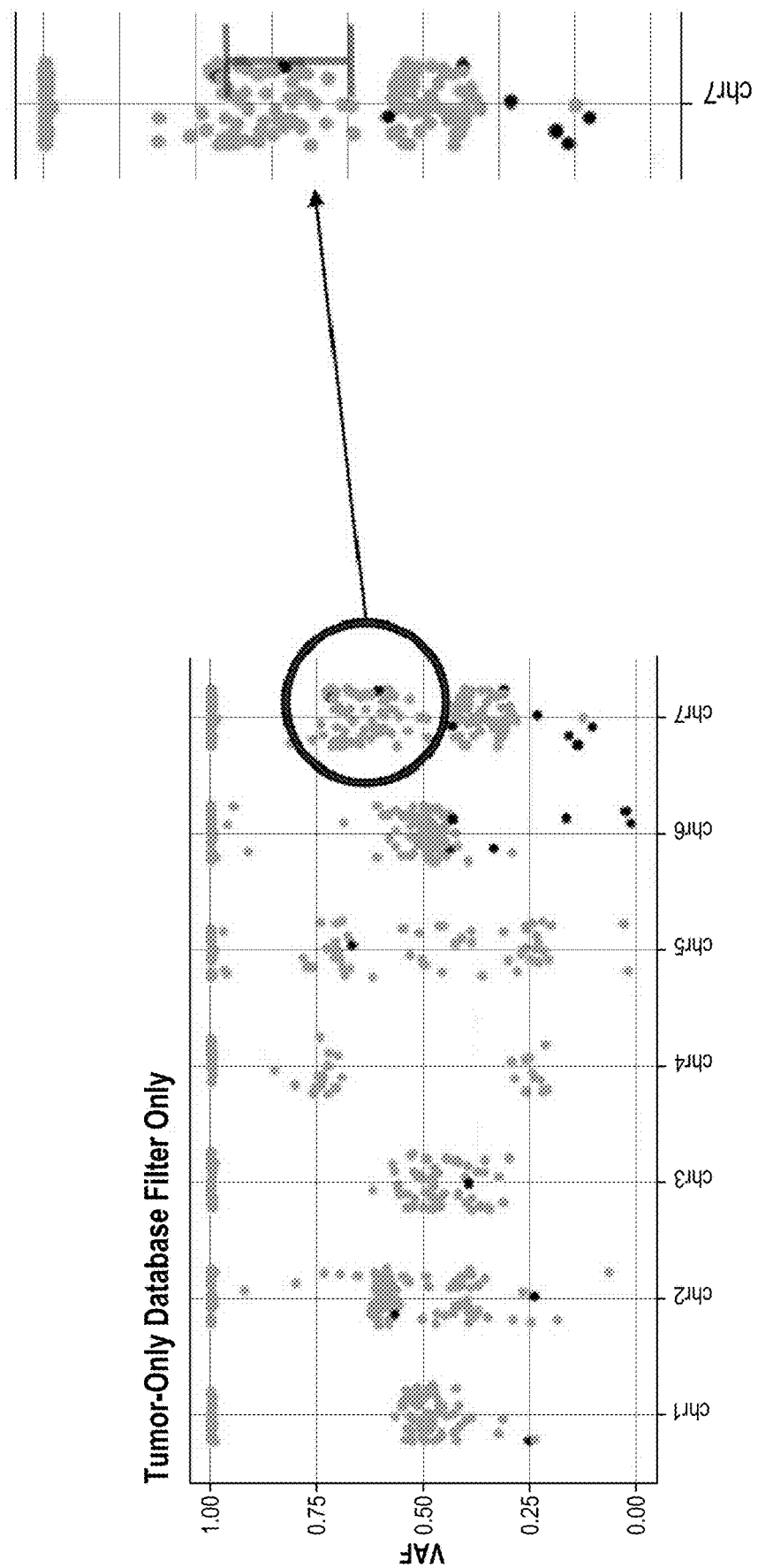
FIG. 3 a graph showing the VAF for various variants according to chromosomal location for chromosomes 1-7 for each variant with filter-determined somatic variants (black-filled circles), and filter-determined germline variants (gray-filled circles), and an enlargement for variants located on chromosome 7 in which a particular filter-determined somatic variant has been selected, and a range drawn from the selected variant.

FIG. 3 (left panel) is a graph showing the variant allele frequency (VAF) for various variants according to chromosomal location for chromosomes 1-7 for each variant with filter-determined somatic variants (black-filled circles), and filter-determined germline variants (gray-filled circles), filtered with a database filter only. FIG. 3 (right panel) is an enlargement for variants located on chromosome 7 in which a particular filter-determined somatic variant (black circle) has been selected, and a range drawn from the variant that encompasses several filter-determined germline variants (gray circle). A determination that the selected filter-determined somatic variant (black circle) should be called as a germline variant can be made based on the proximity of the selected variant's allele frequency to the allele frequencies of a certain number of already identified germline variants.

Figure 4A:
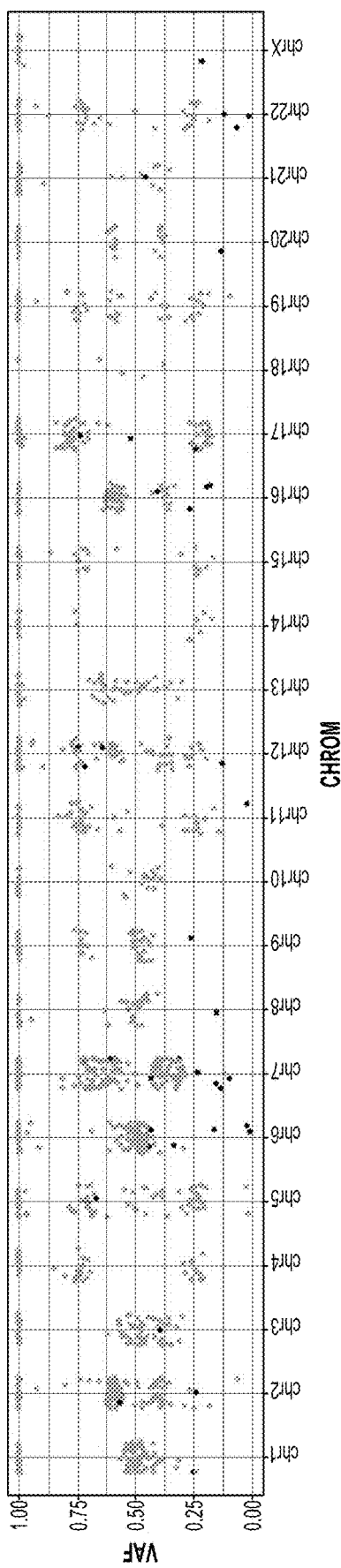
FIG. 4A is a graph showing the VAF for various variants according to chromosomal location of each variant with filter-determined somatic variants (black-filled circles), and filter-determined germline variants (gray-filled circles), filtered with a database filter only.
Figure 4B:
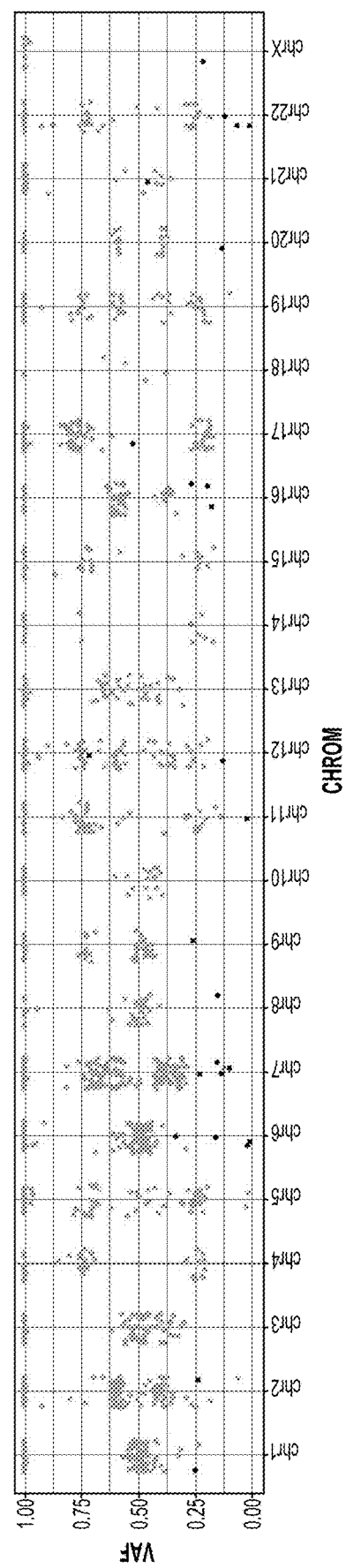
FIG. 4B is a graph showing the VAF for various variants according to chromosomal location of each variant with filter-determined somatic variants (black-filled circles), and filter-determined germline variants (gray-filled circles), filtered with a database filter only, and a proximity filter.

FIG. 4A is a graph showing the variant allele frequency (VAF) for various variants according to chromosomal location of each variant with filter-determined somatic variants (black-filled circles), and filter-determined germline variants (gray-filled circles), filtered with a database filter only. FIG. 4B is a graph showing the variant allele frequency (VAF) for various variants according to chromosomal location of each variant with filter-determined somatic variants (black-filled circles), and filter-determined germline variants (gray-filled circles), filtered with a database filter only, and a proximity filter. FIG. 4B shows that certain putative false positives shown as somatic variants in FIG. 4A, were identified as germline variants in FIG. 4B. For example, identified somatic variants located on chromosome 7 having allele frequencies about 0.4 and 0.3 (FIG. 4A), were identified as germline variants when the proximity filter was applied (FIG. 4B).

Example 4—Measuring Tumor Mutational Burden with Targeted Sequencing

This example relates to a targeted next-generation sequencing assay for measuring tumor mutation burden (TMB) in formalin-fixed, paraffin-embedded (FFPE) tumor samples. FIG. 5 shows an example workflow for the assay. Sequence data was obtained from tumor samples for 523 genes in a panel size of 1.94 Mb with exon size of 1.33 Mb. Sequencing and was performed with unique molecular identifiers (UMIs), and using Illumina NextSeq™ 500/550 platforms. Data analysis was performed using a pipeline for detecting variants at 5% variant allele frequencies (VAF). For technical noise removal, a variant calling algorithm was used that utilized information from UMIs, and sample specific error profiles to ensure a uniform variant calling performance across samples of different FFPE qualities. To accurately remove germline variants from TMB calculations, a hybrid strategy was used that integrated information from large-scale public databases with the measured coverage and variant allele frequency of each variant, and that was substantially similar to the database filter and the proximity filter of the foregoing Examples.

Figure 6:
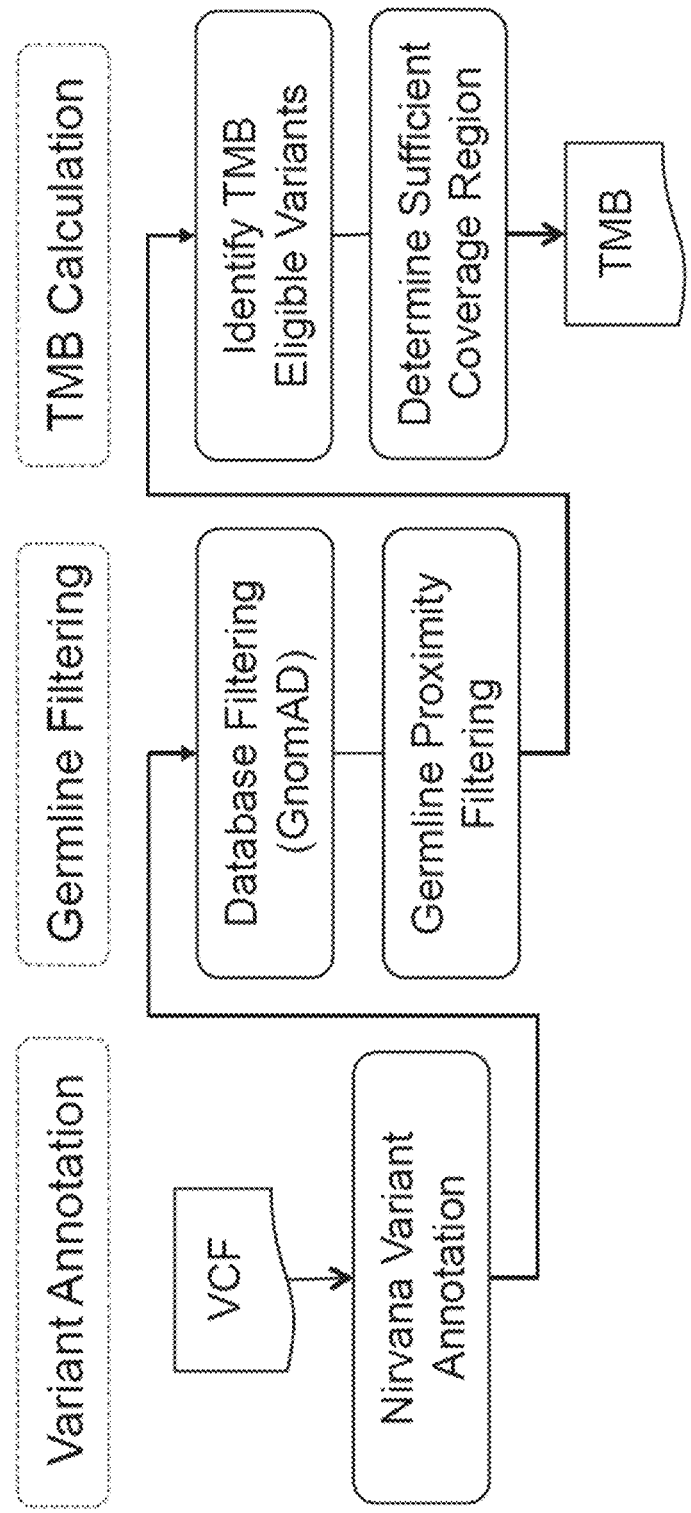
FIG. 6 depicts an example embodiment of a workflow that includes filtering germline variants from the identified variants using a database filter and a proximity filter, and calculating a tumor mutation burden.

Briefly, sequence data was obtained, aligned with a reference, and variants were identified. Germline variants were filtered from the identified variants using a database filter and a proximity filter, and a TMB was calculated in a workflow substantially similar to the pipeline shown in FIG. 6. A total of 170 pairs of tumor-normal samples were analyzed to assess the germline filtering and TMB performance (TABLE 1). A subset of 108 sample pairs were also analyzed with whole exome sequencing (WES).

TABLE 1

| Type | Sample count |
|---|---|
| Colorectal | 74 |
| Lung | 37 |
| Endometrium | 6 |
| Uterine | 32 |
| Gastric | 10 |
| Melanoma | 11 |
| TOTAL: | 170 |

For technical noise removal, the number of false positive variants in a collection of normal FFPE samples (N=176) was assessed. An average of 0.63 false positives per sample, independent of sample quality ($R^2$=0.001) was observed, with 92.6% samples containing ≤2 false positive variants (VAF<20%). In addition, a set of FFPE and cell line mixing samples with variants close to 5% and achieved a sensitivity of 98.7% were tested.

Figure 7:
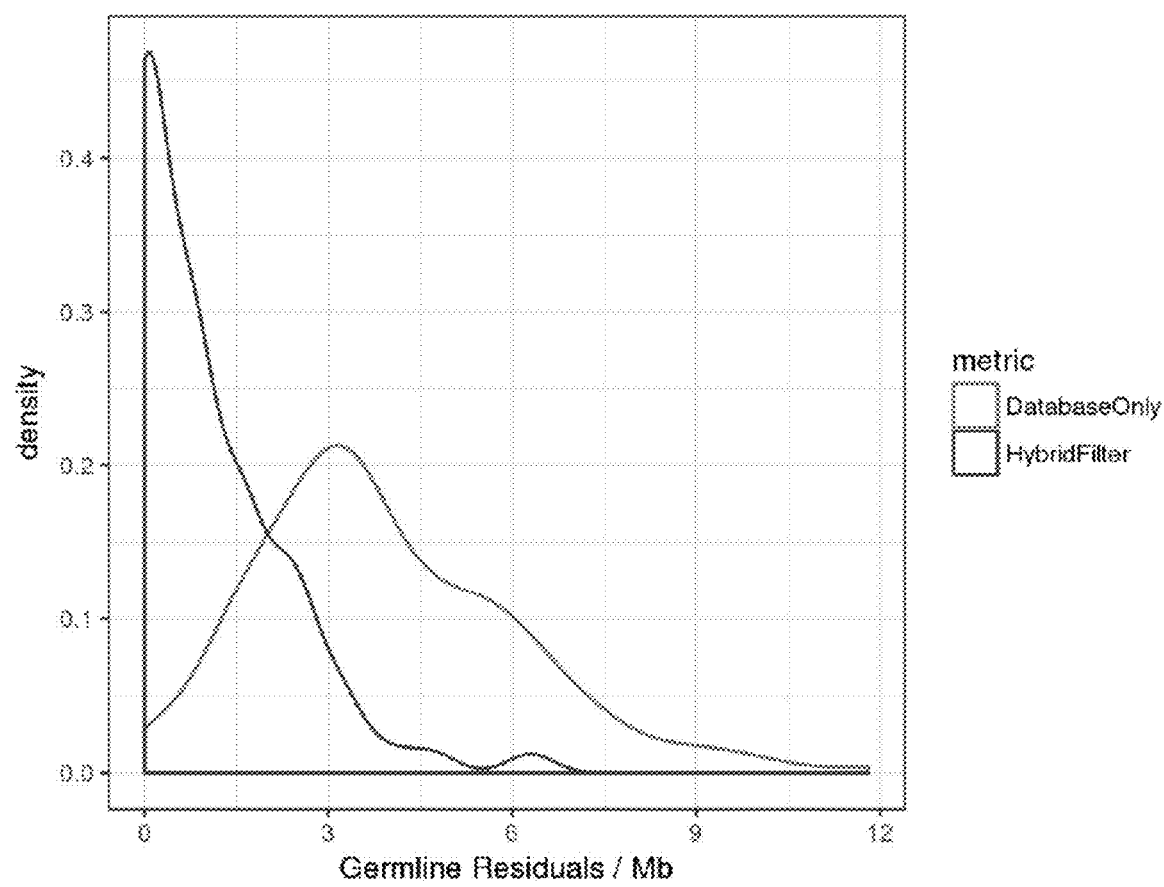
FIG. 7 is a line graph showing a distribution of remaining germline variant count after filtering with database only (graph peaks at about 3 germline residuals/Mb) and the hybrid strategy (graph peaks at about 0 germline residuals/Mb).

The germline filtering performance was assessed using 170 tumor/normal sample pairs described in TABLE 1. In small variant (SNV, insertion/deletion) germline variant filtering, an overall filtering rate above 99.7% was reached which left fewer than 1.3 germline variants on average per sample. The addition of proximity filtering reduced the number of false positives significantly, while only having a minimal effect on somatic mutations. FIG. 7 shows distribution of remaining germline variant count after filtering with database only (graph peaks at about 3 germline residuals/Mb) and the hybrid strategy (graph peaks at about 0 germline residuals/Mb).

TMB reproducibility was assessed in 8 different samples including 4 cell lines and 4 FFPE samples across 3 operators. Mean and standard deviation (SD) of each sample were calculated. TABLE 2 lists TMB reproducibility assessed in 4 cell lines and 4 FFPE samples across 12 replicates each.

TABLE 2

| Sample | DNA type | Replicates | TMB mean | TMB SD |
|---|---|---|---|---|
| T47D | Cell line | 12 | 0.9 | 0.7 |
| H2228 | Cell line | 12 | 7.5 | 0.8 |
| HD799 | Cell line | 12 | 405.0 | 6.8 |
| OncoSpan | Cell line | 12 | 389.1 | 8.4 |
| 1251 | FFPE | 12 | 0.3 | 0.4 |
| 4116 | FFPE | 11 | 24.9 | 0.7 |
| 3643 | FFPE | 12 | 7.6 | 1.4 |
| 4118 | FFPE | 12 | 50.5 | 1.5 |

Figure 8B:
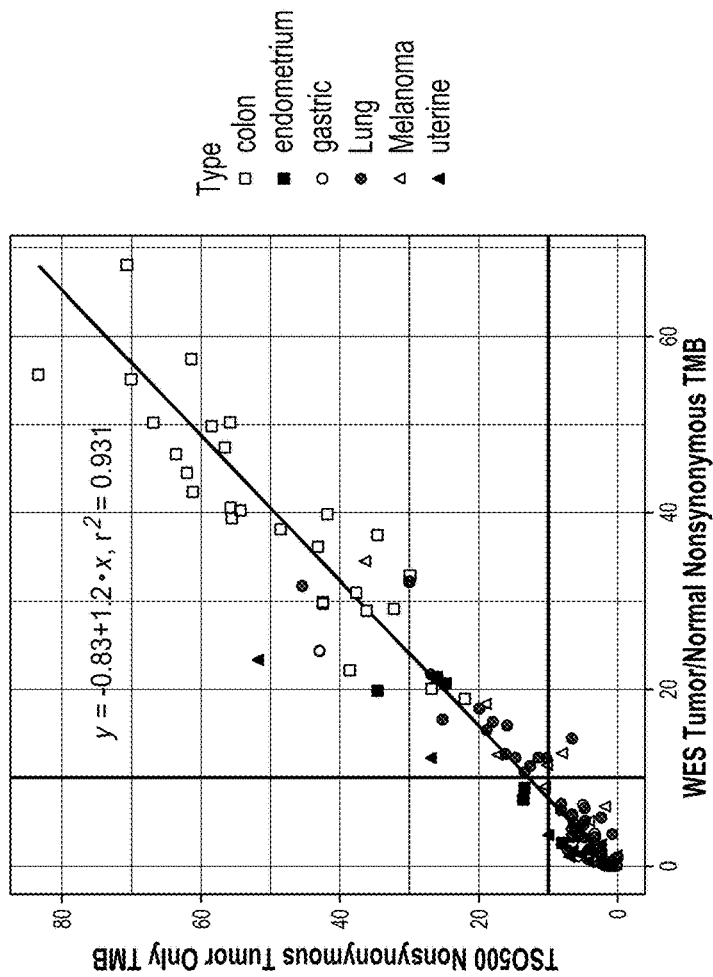
FIG. 8B is a graph showing a comparison of tumor mutation burden (TMB) between tumor-only and WES tumor-normal assays.
Figure 8A:
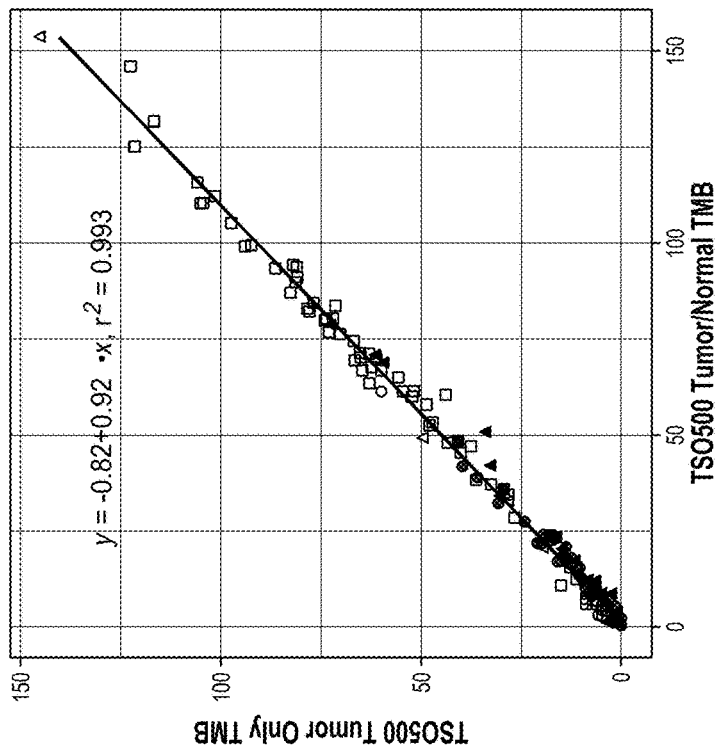
FIG. 8A is a graph showing a comparison of tumor mutation burden (TMB) between tumor-only and tumor/normal assays.

Combined, the TMB measurements generated by tumor only assay highly correlated with estimates generated from tumor/normal assay paired samples ($R^2$=0.993, N=169, TMB<200 samples only). Tumor only assay TMB estimates showed high correlation with TMB values obtained through whole exome sequencing as well ($R^2$=0.931, N=105, WES TMB<100 samples only). FIG. 8A shows TMB comparison between tumor-only and tumor/normal assays. FIG. 8B shows TMB comparison between tumor-only and WES tumor-normal assays.

Finally, with a TMB threshold of 10, a positive percent agreement (PPA) of 94.74% and negative percent agreement (NPA) of 96.08% was demonstrated. The overall classification agreement was 95.37% in distinguishing TMB high and TMB low samples. TABLE 3 lists TMB classification performance.

TABLE 3

|  | WES T/N TMB high | WES T/N TMB low |
|---|---|---|
| TMB high | 54 | 3 |
| TMB low | 2 | 49 |

The foregoing results demonstrated the ability of the assay for tumor only with database and proximity filters to robustly measure TMB in FFPE samples. Furthermore, the TMB estimates showed a high level correlation with WES based measurements with high classification concordance.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of determining a tumor mutation burden of a tumor, comprising:
   obtaining a biological sample comprising tumor cells;
   sequencing DNA from the tumor cells to obtain sequence data;
   aligning the sequence data with a reference sequence to identify a plurality of variants in the sequence data;
   using a computer processor to apply a database filter to the plurality of variants to
   identify first germline variants, comprising:
   identifying variants from the plurality of variants present in a database of variants, wherein the database of variants comprises variants from a plurality of individuals;
   determining if the identified variants have allele counts in the database of variants greater than or equal to a threshold allele count,
   wherein if the identified variants have allele counts in the database of variants greater than or equal to the threshold allele count, the identified variants are first germline variants;
   using a computer processor to apply a proximity filter to the plurality of variants to identify second germline variants, comprising:
   (i) binning variants of the plurality of variants into a plurality of bins, wherein variants located in the same region of a genome are binned into the same bin;
   (ii) identifying variants in the plurality of variants not identified as first germline variants; and
   (iii) retrieving variants from the database of variants located in the same bin and within a threshold proximate range of the variants identified in (ii),
   wherein if the number of retrieved variants within the proximate range of the variants identified in (ii) exceeds a threshold number and if 95% of the retrieved variants within the proximate range of the variants identified in (ii) are first germline variants, the variants identified in (ii) are second germline variants;
   identifying somatic variants in the plurality of variants by removing the first and second germline variants from the plurality of variants; and
   presenting the identified somatic variants on a display, wherein the number of somatic variants per genomic region is the tumor mutation burden of the tumor, and
   treating the tumor by administering an effective amount of a checkpoint inhibitor when the tumor mutation burden is determined.

2. The method of claim 1, wherein the tumor is selected from the group consisting of a colorectal tumor, a lung tumor, an endometrium tumor, a uterine tumor, a gastric tumor, a melanoma, a breast tumor, a pancreatic tumor, a kidney tumor, a bladder tumor, and a brain tumor.

3. The method of claim 1, wherein the checkpoint inhibitor is selected from the group consisting of a CTLA-4 inhibitor, a PD-1 inhibitor, a PD-L1 inhibitor, Ipilimumab, Nivolumab, Pembrolizumab, Spartalizumab, Atezolizumab, Avelumab, and Durvalumab.

4. The method of claim 1, wherein the DNA sequencing is at a depth of at least 100.

5. The method of claim 1, wherein the identifying a plurality of variants in the sequence data further comprises calling variants from a variant calling pipeline.

6. The method of claim 1, wherein the proximate range is a maximum between 0.5 and $2*\sqrt{(100*(\text{allele frequency})*(1-\text{allele frequency})/100}$ from the allele frequency of a second germline variant.

7. The method of claim 1, wherein the threshold allele count is 5 or 10.

8. The method of claim 1, wherein the database of variants from the plurality of individuals comprises at least one database selected from a genome aggregation database, and a 1000 genome database.

9. The method of claim 1, wherein the same region of a genome is within a 10 Mb region.

10. The method of claim 1, wherein the applying a proximity filter further comprises identifying a second germline variant having an allele frequency greater than or equal to 0.9.

11. The method of claim 1, wherein the threshold proximate range is a range having a maximum and a minimum of 0.05 from the allele frequency of a second germline variant.

12. The method of claim 1, wherein the threshold proximate range is a range having a maximum and a minimum of two standard deviations from a binomial distribution of an allele frequency of a second germline variant.

13. The method of claim 1, wherein the second germline variants are within a threshold proximate range of a threshold number of at least five database variants in the same bin.

14. The method of claim 1, wherein the second germline variants are within a threshold proximate range of at least ten database variants in the same bin.

15. The method of claim 1, wherein the biological sample comprising tumor cells is selected from a serum sample, a stool sample, a blood sample, a tumor sample.

16. The method of claim 1, wherein the tumor mutation burden meets or exceeds a tumor mutation burden threshold.

* * * * *

UNITED STATES PATENT AND TRADEMARK OFFICE
CERTIFICATE OF CORRECTION

| | | |
|---|---|---|
| PATENT NO. | : 12,417,819 B2 | Page 1 of 1 |
| APPLICATION NO. | : 16/669270 | |
| DATED | : September 16, 2025 | |
| INVENTOR(S) | : Jin Hyun Ju | |

It is certified that error appears in the above-identified patent and that said Letters Patent is hereby corrected as shown below:

On the Title Page

Column 2, Line 8, under item (56) Other Publications, delete "el" and insert --et--.

Column 2, Line 9, under item (56) Other Publications, delete "nextgeneration" and insert --next generation--.

Column 2, Line 12, under item (56) Other Publications, delete "albiogen-ru" and insert --albiogen.ru--.

In the Drawings

On Sheet 5 of 8, Line 8, FIG. 5, delete "Micosattelite" and insert --Microsatellite--.

In the Specification

In Column 14, Line 55, delete "interfaces(GUIs)" and insert --interfaces (GUIs)--.

In the Claims

In Column 19, Claim 1, Line 11, delete "to identify" and insert --to identify--.

In Column 20, Claim 6, Line 18 (Approx.), delete "frequency)/" and insert --frequency))/--.

Signed and Sealed this
Eighteenth Day of November, 2025

John A. Squires
*Director of the United States Patent and Trademark Office*